USOO5637108A

United States Patent [19]
Vidal et al.

[11] Patent Number: 5,637,108
[45] Date of Patent: Jun. 10, 1997

[54] SURGICAL HANDLE HAVING A CONTROLLED LEAK PASSAGE

[75] Inventors: Claude A. Vidal, Santa Barbara; Russell J. Redmond, Goleta; Alan K. Plyley, Goleta; Michael Collinson, Goleta, all of Calif.; Robert M. Eyerly, Lino Lakes, Minn.

[73] Assignee: United States Surgical Corporation, Norwalk, Conn.

[21] Appl. No.: 260,354

[22] Filed: Jun. 15, 1994

[51] Int. Cl.$^6$ .................................................. A61B 17/00
[52] U.S. Cl. ............................. 606/1; 606/205; 606/140
[58] Field of Search ........................... 606/1, 143, 142, 606/205, 206, 207, 208, 74, 75, 45, 51, 52, 140; 128/749–753

[56] References Cited

U.S. PATENT DOCUMENTS

| | | |
|---|---|---|
| 3,086,208 | 4/1963 | Eby . |
| 3,098,232 | 7/1963 | Brown . |
| 3,638,847 | 2/1972 | Noiles . |
| 3,882,854 | 5/1975 | Hulka et al. . |
| 3,899,914 | 8/1975 | Akiyama . |
| 4,027,510 | 6/1977 | Hiltebrandt . |
| 4,226,239 | 10/1980 | Polk et al. . |
| 4,296,751 | 10/1981 | Blake, III et al. . |
| 4,393,883 | 7/1983 | Smyth et al. . |
| 4,427,014 | 1/1984 | Bel et al. ................................ 606/206 |
| 4,430,997 | 2/1984 | DiGiovanni et al. . |
| 4,452,357 | 6/1984 | Klieman et al. . |
| 4,452,376 | 6/1984 | Klieman et al. . |
| 4,478,220 | 10/1984 | Di Giovanni et al. . |
| 4,500,024 | 2/1985 | DiGiovanni et al. . |
| 4,616,650 | 10/1986 | Green et al. . |
| 4,624,254 | 11/1986 | McGarry et al. . |
| 4,674,504 | 6/1987 | Klieman et al. . |
| 4,800,869 | 1/1989 | Nakajima . |
| 4,850,355 | 7/1989 | Brooks et al. . |
| 4,858,608 | 8/1989 | McQuilkin . |
| 4,985,030 | 1/1991 | Melzer et al. ............................ 606/51 |
| 5,026,379 | 6/1991 | Yoon . |
| 5,030,226 | 7/1991 | Green et al. . |
| 5,040,715 | 8/1991 | Green et al. . |
| 5,084,057 | 1/1992 | Green et al. . |
| 5,100,420 | 3/1992 | Green et al. . |
| 5,151,101 | 9/1992 | Grossi et al. . |
| 5,171,247 | 12/1992 | Hughett et al. . |
| 5,171,249 | 12/1992 | Stefanchik et al. ................ 606/143 X |
| 5,192,288 | 3/1993 | Thompson et al. . |
| 5,207,691 | 5/1993 | Nardella ............................ 606/143 X |
| 5,258,006 | 11/1993 | Rydell et al. ........................... 606/52 |
| 5,279,317 | 1/1994 | Bowman et al. . |
| 5,281,220 | 1/1994 | Blake, III ............................. 606/52 |
| 5,281,230 | 1/1994 | Heidmueller ....................... 606/1 X |
| 5,282,807 | 2/1994 | Knoepfler . |
| 5,282,808 | 2/1994 | Kovac et al. . |
| 5,289,963 | 3/1994 | McGarry et al. . |
| 5,300,081 | 4/1994 | Young et al. ........................... 606/143 |
| 5,314,424 | 5/1994 | Nicholas ............................. 606/1 X |
| 5,334,198 | 8/1994 | Hart et al. ............................. 606/52 |
| 5,356,064 | 10/1994 | Green et al. . |
| 5,364,002 | 11/1994 | Green et al. . |
| 5,382,254 | 1/1995 | McGarry et al. .................... 606/143 |
| 5,382,255 | 1/1995 | Castro et al. . |

FOREIGN PATENT DOCUMENTS

| | | |
|---|---|---|
| 0598529A2 | 5/1994 | European Pat. Off. . |
| 3209444 | 10/1982 | Germany . |
| 9105399 | 9/1991 | Germany . |
| 8904188 | 5/1989 | WIPO . |
| WO90/03763 | 4/1990 | WIPO . |

*Primary Examiner*—Angela D. Sykes
*Assistant Examiner*—Michael Peffley

[57] ABSTRACT

A surgical handle for use with an endoscopic instrument that is insertable into a body cavity insufflated with a gas. The surgical handle includes a housing having a mount that defines an opening for receiving the endoscopic instrument. A first elongated pusher tube is located within the housing and aligned with the mount opening. The pusher tube includes an interior passage that is in fluid communication with the endoscopic instrument. A first actuator moves the pusher tube longitudinally with respect to the mount opening. The interior passage is sized to permit the flow therethrough of insufflation gas escaping from the body cavity up to a predetermined rate, the rate being set at an amount that will not result in deflation of the body cavity.

24 Claims, 2 Drawing Sheets

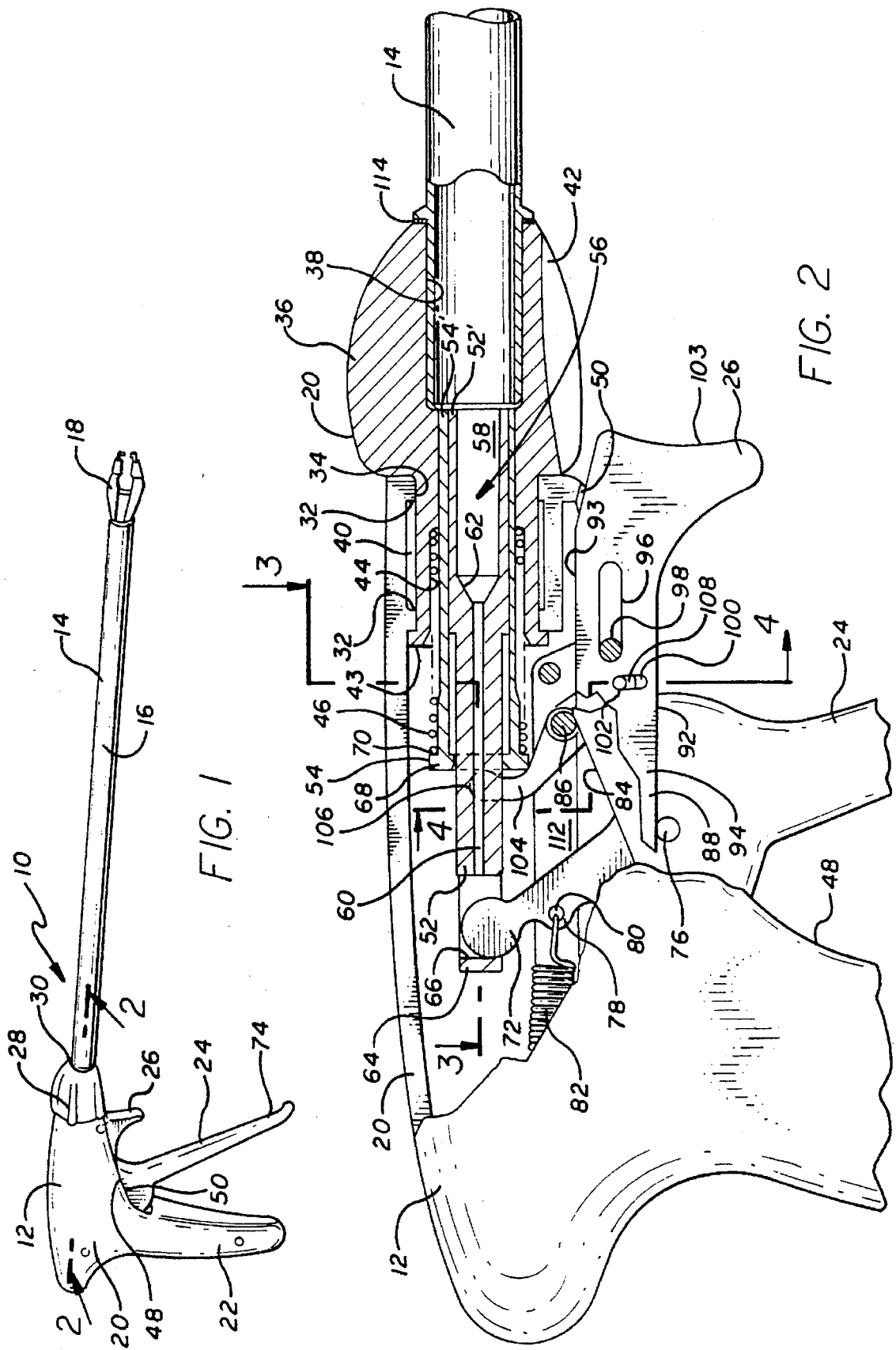

SURGICAL HANDLE HAVING A CONTROLLED LEAK PASSAGE

BACKGROUND OF THE INVENTION

The present invention relates generally to instruments for use in endoscopic or laparoscopic surgery and, more particularly, to a surgical handle having a controlled leak passage.

In laparoscopic surgical procedures, long and narrow instruments are used to perform surgery on tissues and vessels inside an insufflated abdomen through a small incision in the skin. Many laparoscopic instruments require actuation of jaws or other mechanisms on the instrument's distal end inside the abdomen.

For example, a surgical clip applier may be used for applying surgical clips to blood vessels, ducts or the like in laparoscopic or endoscopic procedures. In some cases, the clip applier may have a reusable handle and a disposable endoscopic portion. In such cases, the handle should be designed to permit its thorough cleaning between uses to insure proper mechanical operation and to prevent infection or the like, while the disposable endoscopic portion may be discarded after use.

In U.S. Pat. No. 5,100,420 to Green et al., the endoscopic portion has a long and relatively narrow tube for insertion into a body cavity through a trocar or a small incision. The endoscopic portion includes a pusher bar for advancing surgical clips one at a time to a pair of flexible opposing jaws that close the clips around a vessel or duct. The jaws are clamped together by a distally moving channel. The handle includes a lever for actuating the jaw closing channel and a longitudinally sliding member for actuating the clip advancing pusher bar to load another clip between the jaws. A gaseous seal is provided in the endoscopic portion to prevent communication of gases through the incision. The seal is accomplished by providing close tolerances for the internal moving parts. In a specific embodiment, the gaseous seal includes a seal block with an opening for the pusher bar and the jaw closing channel. The inner surface of the seal block is in close contiguity with the surfaces of the pusher bar and the channel. A layer of silicone grease may be employed to prevent gases from leaking between the surfaces.

Providing a seal by manufacturing parts to close tolerances requires additional time and effort during the manufacture and assembly operations and adds significantly to the cost of the endoscopic portion. In the case of a disposable endoscopic portion, cost is especially important since it is a single use item. In addition, using silicone grease adds to the cost of the item, as well as to its manufacture and assembly.

From the discussion above, it should be apparent that there is a need for a laparoscopic surgical instrument that does not require a seal, but that is still useful in laparoscopic and endoscopic procedures. Additionally, the reusable part of such an instrument should be designed to permit easy cleaning.

SUMMARY OF THE INVENTION

The present invention is embodied in a surgical handle for a laparoscopic or endoscopic instrument, such as a clip applier, that is insertable into an insufflated body cavity. The handle includes a passage for controlling leakage of insufflation gas from the patient during surgery, eliminating the need for a seal in the endoscopic instrument. The passage in the handle is also useful for cleaning the handle after each surgical procedure.

The surgical handle includes a housing having a distal end mount that defines an opening for receiving one end of the endoscopic instrument. The surgical handle also includes a first elongated pusher tube within the housing and aligned with the mount opening. The pusher tube is longitudinally moveable to and from the mount opening and has an interior passage which is in fluid communication with the endoscopic instrument when the endoscopic instrument is received in the mount opening. The surgical handle also includes a first actuator which is configured to move the pusher tube with respect to the mount opening.

A feature of the present invention is that the interior passage of the pusher tube is sized to permit the flow therethrough of insufflation gas escaping from the body cavity up to a predetermined rate, the rate being set at an amount that will not result in deflation of the body cavity. In a preferred embodiment, substantially all of the gas escaping from the body cavity through the endoscopic instrument flows through the interior passage.

In another detailed feature of the present invention, the housing includes a grip and the first actuator includes a lever that is pivotally attached to the housing. The lever has a first end extending away from the housing in a direction generally parallel to and spaced apart from the grip and a second end attached to the proximal end of the inner pusher tube. Accordingly, actuating the lever toward the grip translates the first pusher tube in the direction of the mount opening.

In another feature of the present invention, the surgical handle further includes a second elongated pusher tube located within the housing and oriented coaxially with the first elongated pusher tube. The second elongated pusher tube is longitudinally moveable to and from the mount opening and has an interior passage for receiving the first elongated pusher tube therein. The surgical handle also includes a second actuator configured to move the second elongated pusher tube longitudinally with respect to the mount opening.

In a further feature, the second actuator includes a trigger and a rocker leg. The trigger is configured to slide into the housing when actuated. The rocker leg is pivotally mounted in the housing and has one end engaged with the trigger and its other end engaged with the proximal end of the second elongated pusher tube such that actuating the trigger toward the grip translates the second elongated pusher tube in the direction of the mount opening.

An advantage of the present invention is that the surgical handle may be readily cleaned by forcing cleaning fluid through the interior passage of the first pusher tube to remove any debris or contamination lodged therein.

Other features and advantages of the present invention should become apparent from the following description of the preferred embodiment, taken in conjunction with the accompanying drawings, which illustrate, by way of example, the principles of the invention.

BRIEF DESCRIPTION OF THE DRAWINGS

FIG. 1 is a perspective view of a laparoscopic instrument having a surgical handle of the present invention.

FIG. 2 is a cross-sectional view of the surgical handle of the present invention taken along line 2—2 of FIG.

DESCRIPTION OF THE PREFERRED EMBODIMENT

Figure 3:
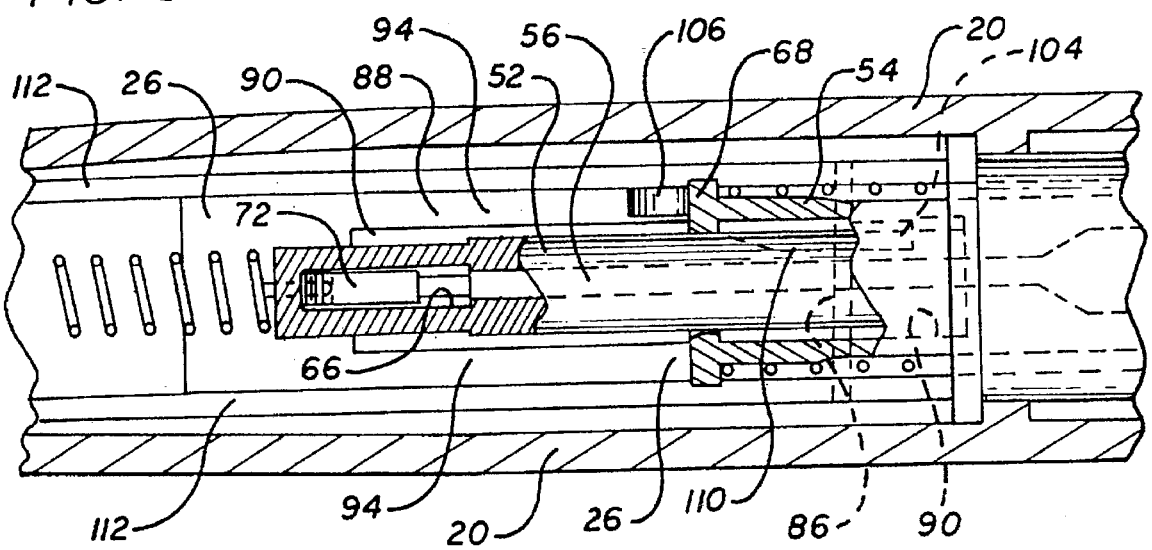
FIG. 3 is a cross-sectional view of the surgical handle taken long line 3—3 of FIG. 2.

With reference now to the drawings and, more particularly, to FIG. 1, there is shown a laparoscopic instrument 10 having a surgical handle 12 and an endoscopic instrument 14. The surgical handle is held in the hand of the surgeon and used to actuate various surgical instruments such as a laparoscopic ligating clip applier. A typical ligating clip applier includes a long cover tube 16 with preloaded clips (not shown) and jaws 18 located at its distal end. The surgeon applies the clips in a two-step process. First, a clip is advanced into the jaws, then the jaws are closed to fasten the clip to a vessel or duct.

In the embodiment shown in FIG. 1, the surgical handle 12 has a hollow housing 20, a grip 22, a lever 24, and a trigger 26. The housing also has a mount 28 at its distal end. The mount defines a circular opening 30 for receiving a proximal end of the endoscopic instrument 14. The grip 22 extends away from the housing 20 in a direction generally perpendicular to the longitudinal axis of the circular opening 30. The housing 20 has two symmetrical halves which are held together by several screws, pins or the like.

In the preferred embodiment, the surgical handle 12 is reusable and the endoscopic instrument 14 is releasably connected to the surgical handle to permit detachment and disposal after use. The trigger 26 and the lever 24 of the handle are operatively connected to the endoscopic instrument to load a clip into the jaws and to close the jaws, respectively A more detailed illustration of the surgical handle 12 is shown in FIG. 2. The distal end of the housing 20 includes a pair of annular flanges 32 defining a bore 34 for receiving the mount 28, which in the preferred embodiment is in the form of a thumbwheel 36. The thumbwheel has an instrument opening 38 therethrough that is sized to receive the end of the endoscopic instrument 14. The thumbwheel has a cylindrical portion 40 that has an exterior diameter sized to be rotatably mounted by the annular flanges 32 in the bore 34 of the housing. This allows a surgeon to rotate the endoscopic instrument 14 so that the jaws can be oriented as desired. A proximal end of the thumbwheel includes an annular lip 43 and an interior annular notch 44. The annular lip 43 engages one of the annular flanges 32 of the housing to prevent pullout after assembly. The interior annular notch 44 receives one end of a first spring 46, the purpose of which will be described in more detail below. The thumbwheel 36 also has a lobed outer surface 42 for ease of turning.

A bottom surface 48 of the housing 20 defines an actuator opening 50 for receiving the lever 24 and the trigger 26, which as mentioned above, are used to actuate the endoscopic instrument. The lever 24 engages a jaw or first elongated pusher tube 52 and the trigger 26 engages a clip or second elongated pusher tube 54. The clip pusher tube has a distal end 54' and the jaw pusher tube has a distal end 52' that may be operatively engaged to corresponding portions (not shown) of the endoscopic instrument for advancing clips into the jaws 18 and closing the jaws, respectively. Various methods of connection are known to those skilled in the art and need not be described herein.

The jaw pusher tube 52 includes an interior passage 56 defined by a distal bore 58, a proximal bore 60 and a short conical section 62 that provides a sloped transition between the distal and proximal bores. The distal bore has a relatively larger diameter than the proximal bore. The interior passage 56 provides a fluid flow passage between the interior of the endoscopic instrument 14 and the interior of the housing. At a proximal end 64 of the jaw pusher tube 52 is a lever trap 66 for receiving the lever 24.

The clip pusher tube 54 is mounted outside of and concentric to the jaw pusher tube 52 and has a flat annular flange 68 at its proximal end. The flange 68 defines an annular shoulder 70 that engages the other end of the previously mentioned first spring 46. The first spring 46 biases the clip pusher tube 54 to a retracted position.

The lever 24 has a first end 72 that is received in the lever trap and engages the jaw pusher tube and a second end 74. The first end 72 is rounded having a disc-like shape to facilitate smooth movement of the jaw pusher tube. The second end 74 (FIG. 1) is long and slender and designed to be engaged by the fingers of the hand. The thickness of the lever 24 is limited by certain dimensions of the trigger 26 discussed below.

The lever 24 is pivotally attached to the housing 20 by a lever pin 76. When attached to the housing 26, the second end of the lever 24 extends out from the housing 20 through the actuator opening 50 in a direction generally parallel to and spaced apart from the grip 22. A tab 78 located between the lever pin 76 and the rounded first end 72 of the lever has a hole 80 by which one end of a second helical spring 82 is connected to the lever. The other end (not shown) of the second helical spring is attached to the housing so as to bias the first end 72 of the lever in a retracted position. The lever 24 also has a ledge 84 that rests against a rocker arm pivot pin 86 mounted to the housing. When assembled, the surgeon actuates the lever by holding the handle 12 with the grip 22 in the palm of one hand and by pulling on the lever with the fingers of that hand. This results in the first end of the lever driving the jaw pusher tube distally. When the surgeon releases the lever, the second spring pulls the lever back to its original position with the ledge resting against the rocker arm pivot pin. The lever trap insures that the return of the lever to its original position will also return the jaw pusher tube to its retracted position.

The trigger 26 has an elongated rectangular shape. With reference to FIGS. 2 and 3, the trigger 26 includes a collar portion 88 that defines a vertically extending opening 90, a bottom surface 92 and a top surface 93. The collar portion 88 includes two laterally spaced walls 94, one on either side of the collar opening 90. At least one of the walls 94 has a first elongated slot 96 for receiving a trigger pin 98 mounted to the housing 20 and a second elongated slot 100, that is disposed perpendicular to the first elongated slot 96, for receiving a rocker arm post 102. The trigger pin 98 vertically locates the distal end of the trigger 26. The length of the first slot 96 limits the trigger's linear movement. The lever pin 76 locates the bottom surface 92 of the trigger and also acts as a guide during trigger actuation. The rocker arm pivot pin 86 locates the top surface 93 of the trigger. A distal end 103 of the trigger has a convenient broadened shape for accommodating the forefinger.

Figure 4:
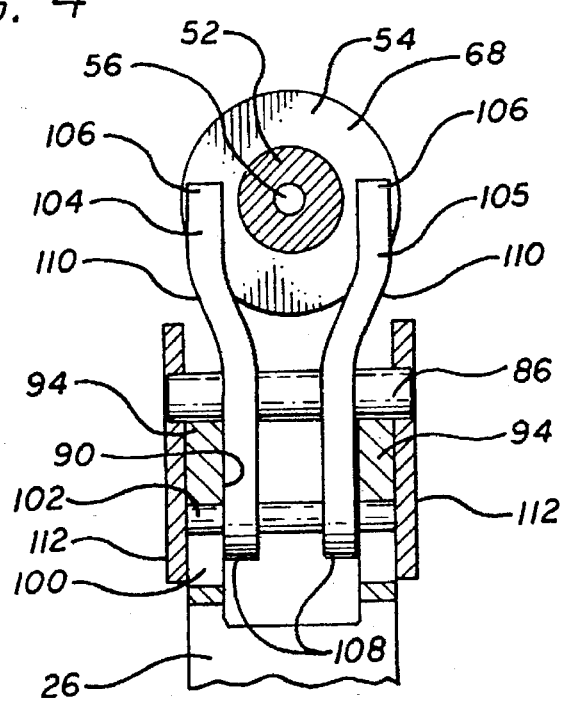
FIG. 4 is a cross-sectional view of the surgical handle taken along line 4—4 of FIG. 2.

With reference to FIGS. 2–4, a rocker arm 104 couples the movement of the trigger 26 to the clip pusher tube 54. The rocker arm 104 is located within the collar opening 90 of the trigger and is pivotally mounted to the rocker arm pivot pin 86. A second rocker arm 105 may also be used (see FIG. 4), if desired, and, in such a case, the rocker arms are mounted in the collar opening 90 of the trigger adjacent respective walls 94 of the trigger.

Each rocker arm has an upper end 106, a lower end 108 and a bend 110 such that the upper end 106 of the rocker arm contacts the annular flange 68 of the clip pusher tube 54 and the lower end 108 of the rocker arm is located in collar opening 90. The rocker arm post 102 is located on the lower end 108 of the rocker arm and is inserted through the second elongated slot 100 of the trigger. Thus, when an operator pulls the trigger, the rocker arm post 102 will traverse the second elongated slot 100 and the rocker arm will pivot about rocker arm pivot pin 86 in a clockwise direction. This results in the upper end 106 of the rocker arm or arms driving the clip pusher tube distally. When the operator releases the lever, the first spring pushes the clip pusher tube to its retracted position. The movement of the clip pusher tube forces the rocker arm or arms and the lever back to their original positions.

It will be appreciated that the lever 24 also passes through the collar opening 90 so that the rounded end 72 of the lever is received in the lever trap 66 (see FIGS. 2 and 3). In the preferred embodiment, metal chassis plates 112 are mounted to the housing to assist in assembly.

In one distinct aspect of the present invention, the surgical handle 12 is used with an endoscopic instrument 14 that has not been provided with an independent seal. Accordingly, communication of gases will occur between the insufflated body cavity, through the endoscopic instrument, into the surgical handle. By providing a gasket 114 between the endoscopic instrument 14 and the thumbwheel 36 (see FIG. 2), gas flow into the handle will occur only through the interior passage 56 of the first pusher tube 52, between the first and second pusher tubes 52, 54 and between the thumbwheel 36 and the second pusher tube 54. Preferably, the size of the interior passage is chosen so that most of the leakage of gas will occur therethrough. In such instances, the size of the interior passage may be used to control the amount of gas flowing out of the insufflated body cavity.

On the one hand, the interior passage 56 should not be so large as to permit a flow rate that is sufficient to deflate the insufflated body cavity. On the other hand, a relatively large flow rate may be desired, e.g., to evacuate the body cavity of smoke caused by certain surgical procedures. Additionally, the passage should preferably be large enough to facilitate cleaning of the handle. In the case of a reusable handle, cleaning may be performed by forcing a cleaning liquid or solution through the interior passage by inserting a hose into the mount opening 30. The interior passage 56 acts as a flushing hole so that any debris or contamination which may have entered into the interior of the pusher tube may be flushed out and removed.

Hypothetical examples of the correlation between the size of the interior passage and the flow rate are provided below. Assuming that the insufflation is provided by carbon dioxide gas of a temperature of 80° F. and a pressure of 14 mm hg (38.8 $lb/ft^2$), the flow rake through an interior passage having the shape of a cylindrically shaped duct having a length of 1.2" and a diameter of 0.02" has been calculated to be about 0.74 liters per minute. A passage of similar length and a diameter of 0.03" will provide a total gas flow rate of about 1.16 liters per minute. Likewise, a passage having the same length with a hole diameter of 0.04" will provide a total gas flow rate of about 2.35 liters per minute. These values will not prematurely deflate the insufflation and are acceptable leak rates based on current insufflator technologies. In the case of a solid first pusher tube, i.e., no interior passage, a small amount of flow would still occur between the first and second pusher tubes and between the second pusher tube and the thumbwheel. In this case, where the parts are made using a standard manufacturing tolerance of ±0.001 inches on the diameters of the tubes, the flow rate has been theoretically calculated to be about 0.19 liters per minute.

To use the surgical handle 12 to apply ligating clips, a disposable endoscopic instrument 14 such as a removable or disposable ligating clip applier cartridge may be inserted into the opening 38 of the thumbwheel 36. The surgeon then first pulls the trigger 26 toward the grip 22. The trigger translates the clip pusher tube 54 by means of the pivotally mounted rocker arm 104. As the trigger is actuated, the rocker arm rotates clockwise and the top or rounded end 106 of the rocker arm pushes against the flange 68 of the clip pusher tube in a direction opposite that of the trigger motion. The distal end 54' of the clip pusher tube engages a mechanism (not shown) in the disposable cartridge instrument which causes a clip to be advanced into the jaws 18. The jaws are closed and the clip applied to a vessel or duct by pulling the lever 24 toward the grip, causing the rounded end 72 of the lever within the lever trap 66 to translate the jaw pusher tube 52 toward the endoscopic instrument, thereby actuating a mechanism (not shown) in the endoscopic instrument which causes the jaws to close on the clip. The lever is connected to the second spring 82 which returns the lever to its original position after the clamping procedure is complete. Likewise, the trigger is returned to its original position by the first spring 46.

The surgical handle 12 provides a reusable surgical device that is advantageous for use during endoscopic or laparoscopic surgical procedures, that is economical to manufacture and that can be thoroughly cleaned after each use. The interior passage 56 included in the reusable handle acts as a flushing hole and also controls the rate of gas flow from an insufflated body cavity.

Although the foregoing discloses preferred embodiments of the present invention, it is understood that those skilled in the art may make various changes to the preferred embodiments shown without departing from the scope of the invention. The invention is defined only by the following claims.

What is claimed is:

1. In a surgical instrument configured for remote actuation within a body cavity maintained in an expanded state by a continuous source of insufflation gas, the surgical instrument including a proximal handle portion and an elongated distal tool portion supported by the handle portion and actuable thereby through a first elongated pusher member mounted for longitudinal movement in the handle portion, the improvement comprising an unobstructed interior passage defined by the first elongated pusher member, the interior passage including a restricted portion configured and dimensioned to control egress of insufflation gas through the handle portion to a predetermined rate which permits maintenance of the expanded state.

2. The instrument of claim 1, wherein the elongated distal tool portion is an endoscopic instrument.

3. The instrument of claim 2, wherein the endoscopic instrument is an elongated clip applier.

4. The instrument of claim 1, further comprising a first actuator configured to move the first elongated pusher tube longitudinally with respect to the opening of the housing.

5. The instrument of claim 4, wherein the first actuator includes a lever pivotally attached to the housing and having a first end extending away from the housing and a second end engaged with a proximal end of the first elongated pusher tube such that actuating the lever moves the first elongated pusher tube in the direction of the opening.

6. The instrument of claim 1, wherein the restricted portion of the interior passage has a length of approximately 1.2 inches and a diameter between approximately 0.02 inches and 0.04 inches.

7. The instrument of claim 1, wherein the interior passage has a circular diameter and is located coaxially through the axis of the first elongated pusher tube.

8. The instrument of claim 1, wherein the interior passage includes a distal bore and a proximal bore and the cross-section of the distal bore being larger than the cross-section of the proximal bore defining the restricted portion.

9. The instrument of claim 8, wherein a short conical section provides a transition between the distal bore and the proximal bore.

10. The instrument of claim 4, further comprising:
   a second elongated pusher tube located within the housing and oriented coaxially with the first elongated pusher tube, the second elongated pusher tube being longitudinally movable with respect to the opening and having an interior passage for receiving the first elongated pusher tube therein; and
   a second actuator configured to move the second elongated pusher tube longitudinally with respect to the opening.

11. A surgical handle adapted for use with an endoscopic instrument that is insertable into a body cavity insufflated with an insufflation gas to an expanded state, the surgical handle comprising:
   a housing having a distal end portion and defining an opening for receiving endoscopic instrument adapted for manipulation by the surgical handle; and
   a first elongated pusher tube located within the housing and aligned with the opening, the first elongated pusher tube being longitudinally movable with respect to the opening and having an unobstructed interior passage for permitting fluid flow through the first elongated pusher tube, the interior passage adapted to be in fluid communication with an endoscopic instrument when positioned in the opening;
   wherein the unobstructed interior passage includes a restricted portion sized to control the flow of insufflation gas exiting therethrough to a predetermined rate which maintain the body cavity in the expanded state.

12. The surgical handle of claim 11, wherein the housing includes a seal to direct the insufflation gas through the interior passage in the first elongated pusher tube.

13. The surgical handle of claim 11 further comprising a first actuator configured to move the first elongated pusher tube longitudinally with respect to the opening of the housing.

14. The surgical handle of claim 13, wherein the first actuator includes a lever pivotally attached to the housing and has a first end extending away from the housing and a second end engaged with a proximal end of the first elongated pusher tube such that actuating the lever moves the first elongated pusher tube in the direction of the opening.

15. The surgical handle of claim 13, further comprising:
   a second elongated pusher tube located within the housing and oriented coaxially with the first elongated pusher tube, the second elongated pusher tube being longitudinally movable with respect to the opening and having an interior passage for receiving the first elongated pusher tube therein; and
   a second actuator configured to move the second elongated pusher tube longitudinally with respect to the opening.

16. The surgical handle of claim 15, wherein the second actuator includes:
   a trigger that slides into the housing when actuated; and
   a rocker leg pivotally mounted in the housing, the rocker leg having a first end that engages the trigger and a second end that engages a proximal end of the second elongated pusher tube such that actuating the trigger causes the rocker leg to move the second elongated pusher tube in the direction of the opening.

17. The surgical handle of claim 11, wherein the size of the interior passage in sufficiently large to permit introduction of a liquid for cleaning the interior passage.

18. The surgical handle of claim 11, wherein the restricted portion of the interior passage has a length of approximately 1.2 inches and diameter between approximately 0.02 inches and 0.4 inches.

19. The surgical handle of claim 11, wherein the interior passage has a circular diameter and is located coaxially through the axis of the first elongated pusher tube.

20. The surgical handle of claim 11, wherein the interior passage includes a distal bore and proximal bore and the cross-section of the distal bore being larger than the cross-section of the proximal bore defining the restricted portion.

21. The surgical handle as defined in claim 20, wherein a short conical section provides a transition between the distal bore and the proximal bore.

22. The surgical handle of claim 11, wherein the opening for receiving an endoscopic instrument is adapted for receiving such instrument in the form of an endoscopic clip applier.

23. A surgical handle adapted for use with an endoscopic instrument that is insertable into a body cavity insufflated with an insufflation gas, the surgical handle comprising:
   a housing having a distal end portion and defining an opening for receiving an endoscopic instrument adapted for manipulation by the surgical handle;
   a first elongated pusher tube located within the housing and oriented coaxially with the opening, the first elongated pusher tube being longitudinally movable with respect to the opening and having an unobstructed interior passage for permitting fluid flow therethrough, the interior passage adapted to be in fluid communication with an endoscopic instrument when positioned in the opening;
   a lever pivotally attached to the housing, the lever having a first end extending away from the housing in a direction generally parallel to and spaced apart from the grip and a second end engaging a proximal end of the first elongated pusher tube such that actuating the lever toward the grip translates the first elongated pusher tube in the direction of the opening;
   a second elongated pusher tube located within the housing and oriented coaxially with the first elongated pusher tube, the second elongated pusher tube being longitudinally movable with respect to the opening and having an interior passage for receiving the first elongated pusher tube therein;
   a trigger that slides into the housing when actuated; and
   a rocker leg pivotally mounted in the housing, the rocker leg having a first end that engages the trigger and a second end that engages a proximal end of the second elongated pusher tube such that actuating the trigger causes the rocker leg to move the second elongated pusher tube in the direction of the opening;
   wherein the unobstructed interior passage is sized to control the flow of the insufflation gas to a predetermined rate.

24. The surgical handle of claim 23, wherein the opening for receiving an endoscopic instrument is adapted for receiving such instrument in the form of an endoscopic clip applier.

* * * * *